United States Patent
Zaima (12)

(10) Patent No.: US 9,266,810 B2
(45) Date of Patent: Feb. 23, 2016

(54) CROSSFLOW TYPE FILTERING OPERATION METHOD USING CERAMIC FILTER

(75) Inventor: Fumiya Zaima, Okayama (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 204 days.

(21) Appl. No.: 13/881,022

(22) PCT Filed: Oct. 25, 2011

(86) PCT No.: PCT/JP2011/074573
§ 371 (c)(1),
(2), (4) Date: Jul. 9, 2013

(87) PCT Pub. No.: WO2012/057156
PCT Pub. Date: May 3, 2012

(65) Prior Publication Data
US 2013/0289303 A1  Oct. 31, 2013

(30) Foreign Application Priority Data

Oct. 26, 2010 (JP) .................................. 2010-239665
Oct. 26, 2010 (JP) .................................. 2010-239666

(51) Int. Cl.
| | |
|---|---|
| *C07C 51/47* | (2006.01) |
| *B01D 71/02* | (2006.01) |
| *B01D 61/14* | (2006.01) |
| *B01D 65/02* | (2006.01) |
| *B01D 63/06* | (2006.01) |

(52) U.S. Cl.
CPC .............. *C07C 51/47* (2013.01); *B01D 61/145* (2013.01); *B01D 65/02* (2013.01); *B01D 71/024* (2013.01); *B01D 63/066* (2013.01); *B01D 2321/04* (2013.01)

(58) Field of Classification Search
None
See application file for complete search history.

(56) References Cited

U.S. PATENT DOCUMENTS

| 4,957,625 | A | | 9/1990 | Katoh | |
|---|---|---|---|---|---|
| 5,955,394 | A | * | 9/1999 | Kelly | ............................... 502/12 |

(Continued)

FOREIGN PATENT DOCUMENTS

| DE | 3525230 | 1/1987 |
|---|---|---|
| EP | 1 224 029 | 7/2002 |
| JP | 53-102290 | 9/1978 |

(Continued)

OTHER PUBLICATIONS

English Translation of Yamada et al. JP 03131312, 1991.*

(Continued)

*Primary Examiner* — Sudhakar Katakam
*Assistant Examiner* — Jennifer C Sawyer
(74) *Attorney, Agent, or Firm* — Greenblum & Bernstein, P.L.C.

(57) ABSTRACT

Provided is a simple filtering operation method capable of conducting a filtering operation without clogging in a ceramic filter for a long period of time, in the operation of filtering fine crystals of an aromatic carboxylic acid in an oxidation reaction mother liquor obtained in a process of an aromatic carboxylic acid production by a cross-flow filtration using the ceramic filter. The present invention can be accomplished by conducting an operation for filtering the fine crystals and a back washing operation with a filtrate while maintaining a flowing circulation operation of the oxidation reaction mother liquor under predetermined conditions.

12 Claims, 3 Drawing Sheets

(56) References Cited

U.S. PATENT DOCUMENTS 6,307,099 B1   10/2001   Turner
6,692,786 B1   2/2004    Denk et al.

FOREIGN PATENT DOCUMENTS

| JP | 63-51913 | 3/1988 |
|---|---|---|
| JP | 3-131312 | 6/1991 |
| JP | 5-317024 | 12/1993 |
| JP | 9-239246 | 9/1997 |
| JP | 10-15390 | 1/1998 |
| JP | 2000-140842 | 5/2000 |
| JP | 2002-12573 | 1/2002 |
| JP | 2002-263412 | 9/2002 |
| JP | 2003-507160 | 2/2003 |
| WO | WO 98/38150 | 9/1998 |
| WO | WO 98/41478 | 9/1998 |
| WO | 01/10540 | 2/2001 |
| WO | WO 01/12318 | 2/2001 |
| WO | 2008/072561 | 6/2008 |
| WO | 2008/075572 | 6/2008 |

OTHER PUBLICATIONS

Invitation to Respond to Written Opinion dated Oct. 13, 2014, which attaches the Written Opinion and Search and Examination Report for Singaporean Application No. 201303149-7, which were both mailed on Aug. 14, 2014.
U.S. Appl. No. 13/881,021 to Fumiya Zaima et al., filed Apr. 23, 2013.
International Search Report in /PCT/JP2011/074573, mailed Jan. 31, 2012.
Article entitled Membrane backwashing in Membrane Technology and Applications, Jan. 2004 by R. W. Baker, XP055183922.
Article entitled Methods Employed for Control of Fouling in MF and UF Membranes: A Comprehensive Review in Separation Science and Technology, col. 40, No. 10, Jan. 2005. pp. 1957-2005, XP008169191.
EPO Search Report issued in EP 11836289 and dated May 15, 2015.

* cited by examiner

CROSSFLOW TYPE FILTERING OPERATION METHOD USING CERAMIC FILTER

TECHNICAL FIELD

The present invention relates to a filtering operation method of a ceramic filter used in solid-liquid separation for removing fine crystals contained in an oxidation reaction mother liquor obtained in a process for producing an aromatic carboxylic acid to obtain a clear filtrate.

BACKGROUND ART

Aromatic carboxylic acids are produced by liquid-phase oxidation reaction of alkyl group-containing aromatic hydrocarbons. In this reaction, a heavy metal catalyst such as cobalt and manganese, or the catalyst to which a promoter such as a bromine compound and an aldehyde is further added is usually used in the presence of an acetic acid solvent.

An aromatic carboxylic acid-containing slurry obtained from such a liquid-phase oxidation reaction is usually subjected to crystallization to reduce its temperature and then subjected to solid-liquid separation under a pressure close to normal pressures to thereby obtain a cake of an aromatic carboxylic acid.

On the other hand, an oxidation reaction mother liquor obtained in the solid-liquid separation contains useful catalyst components derived from the catalyst such as heavy metal ions and bromide ions. When industrially practicing the above reaction, it is necessary to recycle and reuse these catalyst components and thereby reduce production costs.

The simplest recycling method is a method in which the oxidation reaction mother liquor is fed as itself back to a reaction system and reused therein (mother liquor recycling), and this method has been extensively used in commercial production processes. However, the oxidation reaction mother liquor contains various organic impurities by-produced in the liquid-phase oxidation reaction or inorganic impurities produced owing to corrosion of an apparatus used. If the oxidation reaction mother liquor is reused as itself in the reaction system, the concentration of these impurities in the reaction system tends to be gradually increased. As a result, it has been confirmed that when the concentration of the impurities exceeds a predetermined level, the liquid-phase oxidation reaction tends to be adversely affected.

For example, it has been reported that if the aromatic carboxylic acid is isophthalic acid, the proportion of the oxidation reaction mother liquor fed back to the reaction system (mother liquor recycling rate) is usually from 60 to 90%. The remaining oxidation reaction mother liquor which does not serve for reuse in the reaction system and is present in an amount of from 10 to 40% is fed to a step of recovering acetic acid as a solvent (the mother liquor not fed back to the reaction system is called a "purge mother liquor"). Also, it has been reported if the aromatic carboxylic acid is 2,6-naphthalenedicarboxylic acid, the proportion of the oxidation reaction mother liquor fed back to the reaction system is usually from 30 to 90%. The remaining oxidation reaction mother liquor which does not serve for reuse in the reaction system and is present in an amount of from 10 to 70% is fed to a step of recovering acetic acid as a solvent.

As a method of recovering the catalyst components from the oxidation reaction mother liquor fed to the acetic acid recovering step and reusing it, there have been proposed the method using an anion-exchange resin (Patent Documents 1 to 4) and the method using a pyridine ring-containing chelate resin (refer to Patent Documents 5 and 6).

In Patent Document 2, it is described that an oxidation reaction mother liquor contains fine aromatic carboxylic acid crystals leaked from an aromatic carboxylic acid slurry upon solid-liquid separation thereof or precipitated by temperature drop of the oxidation reaction mother liquor, and therefore when continuously feeding the oxidation reaction mother liquor to a resin column to contact with a resin, it is necessary to remove the fine crystals using a filter, etc., in order to prevent deposition of the fine crystals on an upper portion or an inside portion of a resin layer. However, Patent Document 2 fails to describe a specific method for removing the fine crystals. In Patent Document 3, it is described that solids need to be removed by filtering the oxidation reaction mother liquor in advance, at a temperature not higher than a temperature of the operation. Although an installation place of a high-grade filter for removing the fine crystals is specified in a schematic flow-diagram of the process, details of the filter itself is not described. In Patent Documents 5 and 6, it is described that an oxidation reaction slurry is preferably subjected to solid-liquid separation such that a content of crystals in the oxidation reaction mother liquor is 0.1% or less, but a filter for removing the fine crystals is not described.

In Patent Document 4, it is described that a mother liquor purge flow is filtered through a filter medium to recover and recycle an insoluble aromatic carboxylic acid and the other insoluble components. As examples of the filter medium, there are mentioned a microfiltration filter medium, an ultrafiltration filter medium, a membrane filter medium, a cross-flow filter medium, a hydro-cyclone filter medium, a cross-flow ceramic microfiltration filter medium, a bag filter medium, a sintered metal cross-flow ceramic microfiltration filter medium, a cross-flow microfiltration filter medium or the like. It is also described that among these filter media the cross-flow filtration using an anticorrosive and high temperature-resistant ceramic filter is preferred because the aromatic carboxylic acid as a product material trapped on the filter medium can be continuously removed and recovered. However, details of the filtering operation are not disclosed, and it is merely described that a suitable turbulence is obtained when a Reynolds number of a fluid entering into a flow path of the ceramic filter is larger than about 13,000.

When the an oxidation reaction mother liquor containing fine crystals is processed by a cross-flow filtration method using a ceramic filter, the fine crystals deposited on a filtering membrane of the ceramic filter are filtered while always washing out with a circulating fluid flowing through a flow path to obtain a clear filtrate. However, since a filtering performance is gradually deteriorated owing to deposition of the fine crystals, it is required to interrupt the filtering operation to clean the ceramic filter.

As the method of the cleaning, there may be used a method in which the cleaning is conducted by interrupting circulation of the oxidation reaction mother liquor flowing through the flow path of the ceramic filter, or a method in which it is conducted while continuing the circulation thereof.

In the method in which the circulation is interrupted, in order to remove the deposited fine crystals, a wash solvent capable of dissolving the fine crystals (specifically, for example, an acetic acid solvent) flows through the flow path of the ceramic filter to clean a surface of the filtering membrane, and the wash solvent flows from the flow path side to the filtration side to penetrate through the filtering membrane (normal washing with the wash solvent). In addition, the wash solvent is effectively made to penetrate from the filtration side to the flow path side of the ceramic filter (back washing with the wash solvent). Thus, by using the method in which the circulation is interrupted, it is possible to fully clean the ceramic filter and completely restore a filtering performance thereof (refer to Patent Documents 7 and 8). However, the method in which the circulation is interrupted has various problems such as need of using a large amount of the wash solvent, time-consuming procedure, complicated valve operations upon feed and interruption of the oxidation reaction mother liquor as well as upon feed and interruption of the wash solvent, occurrence of treatment of a large amount of the used wash solvent, and so on.

In the method of cleaning the ceramic filter in which the circulation of the oxidation reaction mother liquor is not interrupted, a filtrate is allowed to penetrate from the filtration side to the flow path side of the ceramic filter (back washing with the filtrate). This method requires no fresh wash solvent (producing no used wash solvent) and can be easily conducted only by interrupting the filtering operation, so that a filtering performance of the ceramic filter can be substantially restored. Therefore, the above method has been frequently employed in filtering operations by a ceramic filter in a general cross-flow type (refer to Patent Documents 9 and 10).

In Patent Document 9, it is described that while circulating a stock solution, a pressure higher than that on the stock solution side is instantaneously applied onto a filtrate in a filter container by a piston, and the filtrate is forced into the filter at a linear velocity larger than the filtering linear velocity to conduct the back washing operation of the filter. This method is characterized in that the back washing time is very short.

From the contents of Examples in this document, it is construed that the feature of the method resides in that when the filtering linear velocity is lowered owing to clogging of the filter, the back washing operation with the filtrate is conducted at a linear velocity larger than such a lowered filtering linear velocity.

However, the above method has posed problems such as use of the piston facility when industrially practiced. Further the differential pressure applied upon the back washing operation is not described.

In claim 7 of Patent Document 10, it is described that a filtrate is reversely flowed from an outer periphery side to a flow path side of a filter to remove particles fixed on a surface of a filtering membrane. In addition, in the specification, it is described that upon conducting the cross-flow filtration, a periodic back washing is preferably performed in order to prevent fixing of a cake layer on the surface of the filtering membrane. There is mentioned such a back washing mechanism that a sump for back washing (back washing pot) is provided on a recovery side of the filtrate, and the filtrate is reversely flowed toward the flow path side by an air compressor or a pump. Further, in Example, as shown in FIG. 1, there is illustrated a structure including the air compressor and the back washing pot, which is capable of reversely flowing the filtrate from the outer periphery side of the filter to the flow path side thereof.

However, any of these Patent Documents merely describe a general back washing, but fail to describe requirements for efficiently conducting the back washing operation. Also, as the back washing with the filtrate is repeated, a recovery rate of a filtering performance is gradually lowered so that the filter finally fails to exhibit a desired filtering performance. In such a case, after the circulation of the oxidation reaction mother liquor is interrupted, the ceramic filter should be cleaned by normal washing with the wash solvent and/or back washing with the wash solvent.

PRIOR ART DOCUMENTS

Patent Documents

Patent Document 1: JP 53-102290A
Patent Document 2: JP 10-15390A
Patent Document 3: JP 2002-12573A
Patent Document 4: JP 2003-507160A
Patent Document 5: WO 2008/072561A
Patent Document 6: WO 2008/075572A
Patent Document 7: JP 3-131312A
Patent Document 8: JP 5-317024A
Patent Document 9: JP 63-51913A
Patent Document 10: JP 2000-140842A

SUMMARY OF THE INVENTION

Problem to be Solved by the Invention

Thus, in the operation for filtering fine aromatic carboxylic acid crystals contained in an oxidation reaction mother liquor by a cross-flow filtration using a ceramic filter in an aromatic carboxylic acid production process, there is still present such a problem that the following filtering operation methods have not been found yet:

(1) a simple filtering operation method in which the filtering operation with the ceramic filter can be conducted by the cross-flow filtration for a long period of time without clogging; and (2) a filtering operation method in which no use of a large amount of a wash solvent is required.

Means for Solving the Problem

As a result of extensive and intensive researches for achieving the above object, the present inventors have found a stable and simple filtering operation method and have accomplished the present invention.

That is, the present invention relates to the following aspects (1) to (8).

(1) A filtering operation method for filtering fine crystals contained in an oxidation reaction mother liquor obtained in a process for producing an aromatic carboxylic acid except for terephthalic acid by a cross-flow filtration using a ceramic filter while conducting a flowing circulation operation of the oxidation reaction mother liquor, the method comprising:

conducting (I) an operation for filtering the fine crystals; and conducting (II) a back washing operation with a filtrate while maintaining the flowing circulation operation of the oxidation reaction mother liquor, (II) the back washing operation with the filtrate being conducted under the following conditions:

(II-A) an operation time thereof that is in the range of from 5 to 60 [s];

(II-B) a differential pressure between a filtration side and a flow path side of the ceramic filter which is in the range of from 0.10 to 1.0 [MPa];

(II-C) a feeding linear velocity of the filtrate that is in the range of from 1.0 to 20 [m/h]; and (II-D) a temperature of the filtrate that is in the range of from "a temperature of the oxidation reaction mother liquor" to "a temperature higher by 35° C. than that of the oxidation reaction mother liquor".

(2) The filtering operation method as described in the above aspect (1), wherein (I) the operation for filtering the fine crystals is carried out under the following conditions:

(I-A) an operation time which is in the range of from 60 to 1800 [s];

(I-B) a differential pressure between the flow path side and the filtration side that is in the range of from 0.05 to 0.5 [MPa];

(I-C) a circulating linear velocity of the oxidation reaction mother liquor in the flow path of the ceramic filter that is in the range of from 1000 to 10000 [m/h] as measured at an inlet of the flow path; and (I-D) a filtering linear velocity of the filtrate that is in the range of from 0.5 to 3.0 [m/h].

(3) The filtering operation method as described in the above aspect (1) or (2), further comprising: conducting (III) a back washing operation with a wash solvent while maintaining the flowing circulation operation of the oxidation reaction mother liquor.

(4) The filtering operation method as described in the above aspect (3), wherein (III) the back washing operation with the wash solvent is conducted under the following conditions:

(III-A) an operation time thereof that is in the range of from 5 to 120 [s];

(III-B) a differential pressure between the filtration side and the flow path side upon the back washing operation with the wash solvent that is in the range of from 0.10 to 1.0 [MPa];

(III-C) a feeding linear velocity of the wash solvent upon the back washing operation that is in the range of from 1.0 to 20 [m/h]; and (III-D) a temperature of the wash solvent that is in the range of from "the temperature of the oxidation reaction mother liquor" to "the temperature higher by 35° C. than that of the oxidation reaction mother liquor".

(5) The filtering operation method as described in the above aspect (3) or (4), wherein an operation comprising (I) the operation for filtering the fine crystals and (II) the back washing operation with the filtrate is repeated, and when a flow rate of the filtering operation is not restored by (II) the back washing operation with the filtrate, (III) the back washing operation with the wash solvent is conducted.

(6) The filtering operation method as described in any one of the above aspects (3) to (5), wherein the wash solvent is acetic acid having a water content of from 0.1 to 30% by mass.

(7) The filtering operation method as described in any one of the above aspects (1) to (6), wherein upon the back washing operation with the filtrate, a pressure on a circulation outlet conduit side of the ceramic filter is reduced to produce a differential pressure thereby feeding the filtrate.

(8) The filtering operation method as described in any one of the above aspects (1) to (7), wherein the aromatic carboxylic aid comprises at least one of benzoic acid, phthalic acid, isophthalic acid, m-toluic acid, trimesic acid, 3,5-dimethyl benzoic acid, trimellitic acid, pyromellitic acid, 1,5-naphthalenedicarboxylic acid and 2,6-naphthalenedicarboxylic acid.

Effect of the Invention

It has been found that when fine crystals contained in an oxidation reaction mother liquor in an aromatic carboxylic acid production process are subjected to the cross-flow filtration using a ceramic filter, due to the operation under limited conditions, it is possible to attain the following effects:

(1) a filtering operation can be simply performed for a long period of time without clogging of the ceramic filter;

(2) no use of a large amount of a wash solvent is needed; and (3) an aromatic carboxylic acid contained in the wash solvent which has been conventionally discarded together with the wash solvent upon cleaning can be recovered.

PREFERRED EMBODIMENTS FOR CARRYING OUT THE INVENTION

Figure 1:
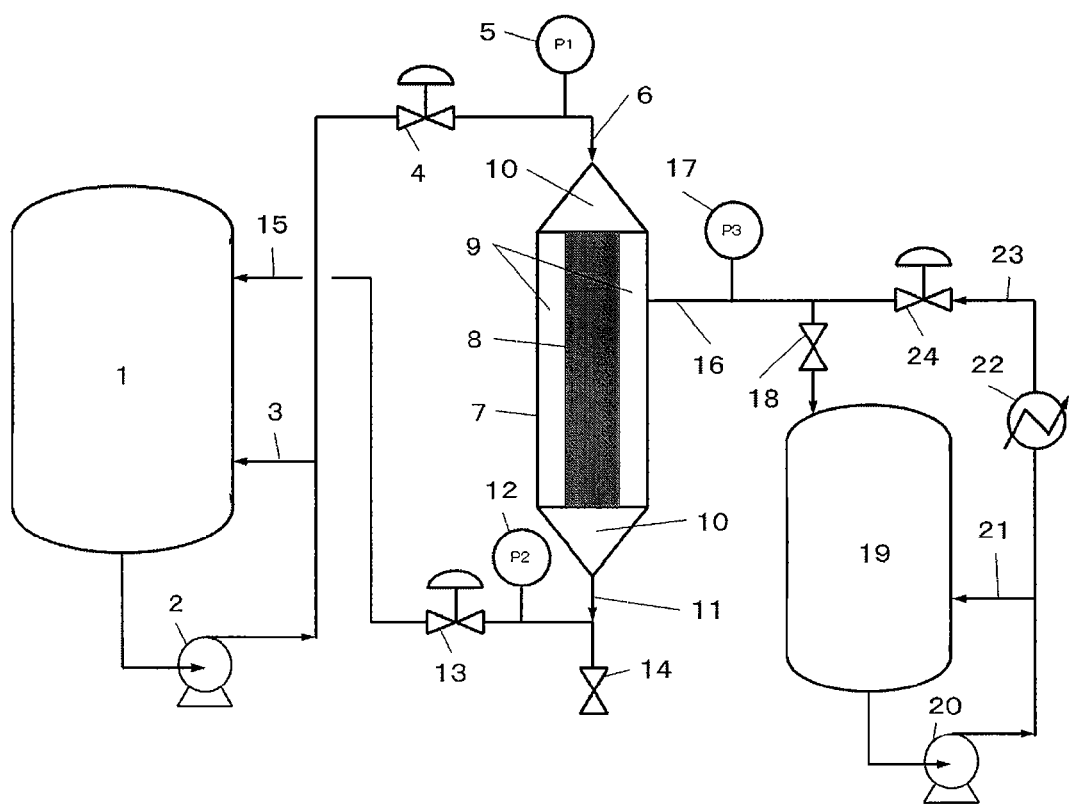
FIG. 1 is a pipeline diagram showing an embodiment of the present invention.

The aromatic carboxylic acid as described in the present invention is a compound produced by liquid-phase oxidation of an alkyl group-containing aromatic hydrocarbon. The alkyl group-containing aromatic hydrocarbon may be a compound having an aromatic ring to which at least one methyl substituent group is bonded, and the aromatic ring may be either an aromatic hydrocarbon ring or an aromatic heterocyclic ring. Specific examples of the alkyl group-containing aromatic hydrocarbon include toluene, o-xylene, m-xylene, 1,3,5-trimethyl benzene, 1,2,4-trimethyl benzene, 1,2,4,5-tetramethyl benzene, 2,4-dimethyl benzaldehyde, 3,4-dimethyl benzaldehyde, 2,4,5-trimethyl benzaldehyde, 1,5-dimethyl naphthalene 2,6-dimethyl naphthalene, and so on.

Specific examples of the aromatic carboxylic acid obtained by liquid-phase oxidation of the alkyl group-containing aromatic hydrocarbon include benzoic acid, phthalic acid, isophthalic acid, m-toluic acid, trimesic acid, 3,5-dimethyl benzoic acid, trimellitic acid, pyromellitic acid, 1,5-naphthalenedicarboxylic acid and 2,6-naphthalenedicarboxylic acid, and so on. However, terephthalic acid is excluded from the aromatic carboxylic acid.

In the liquid-phase oxidation reaction of the alkyl group-containing aromatic hydrocarbon, a heavy metal compound and a bromine compound are used as catalysts.

The heavy metal compound as the liquid-phase oxidation reaction catalyst contains at least one of a cobalt compound and a manganese compound, and if required a nickel compound, a cerium compound, a zirconium compound, and so on may be further added thereto. The cobalt compound, the manganese compound and the other heavy metal compounds may be respectively used, for example, in the form of an organic acid salt, a hydroxide, a halide, a carbonate or the like. Among these, especially preferred are an acetic acid salt and a bromide.

The concentration of the heavy metal compound is defined by a concentration thereof in the oxidation reaction mother liquor, and not particularly limited as long as it lies within the range capable of accelerating the liquid-phase oxidation reaction. For example, the concentration of cobalt ions is usually 100 ppm or more and preferably 200 ppm or more, and the upper limit thereof is 6000 ppm or less and preferably 5000 ppm or less. Also, the concentration of manganese ions is usually 100 ppm or more and preferably 150 ppm or more, and the upper limit thereof is 3000 ppm or less and preferably 2500 ppm or less.

The bromine compound as the liquid-phase oxidation reaction catalyst may be any bromine compound as long as it is capable of being dissolved in the reaction system and generating bromide ions. Examples thereof include inorganic bromine compounds such as hydrogen bromide, sodium bromide and cobalt bromide, and organic bromine compounds such as bromoacetic acid and tetrabromoethane. Especially, hydrogen bromide, cobalt bromide or manganese bromide is suitable.

The concentration of the bromine compound used is defined by a concentration thereof in the oxidation reaction mother liquor, and not particularly limited as long as it lies within the range capable of accelerating the liquid-phase oxidation reaction. For example, the concentration of bromide ions is usually 300 ppm or more and preferably 500 ppm or more, and the upper limit thereof is 7000 ppm or less and preferably 6000 ppm or less.

The temperature of the liquid-phase oxidation reaction is preferably in range from 120 to 230° C. and more preferably from 140 to 210° C. When the reaction temperature is excessively low, a large amount of intermediate reaction products tend to remain in the resulting slurry. When the reaction temperature is excessively high, the acetic acid having a water content of from 1 to 15% by mass as a solvent tends to exhibit a large combustion loss.

The pressure in a reactor used in the liquid-phase oxidation reaction is not particularly limited as long as the reaction system is capable of maintaining a liquid-phase at the reaction temperature, and is usually from 0.1 to 3.0 [MPaG] and preferably from 0.3 to 1.8 [MPaG].

Examples of a molecular oxygen-containing gas that is used as an oxidizing agent in the liquid phase oxidation reaction include air, inert gas-diluted oxygen and oxygen-rich air, but in view of facilities and costs the use of air is usually preferred.

The oxidation reaction slurry containing crude aromatic carboxylic acid crystals which is produced in an oxidation reactor used in the liquid-phase oxidation reaction is preferably fed to a next oxidation reactor connected in series thereto, and is further subjected to final oxidation reaction with an oxygen-containing gas. After that, following dropping pressure and cooling through crystallization vessels having one or more stages which are connected in series if required, then the slurry is fed to the subsequent solid-liquid separation step.

An example of the liquid-phase oxidation reaction is as follows. For example, using an apparatus with a commercial scale, m-xylene is subjected to liquid-phase oxidation by air (reaction temperature: 200 [° C.]; reaction pressure: 1.6 [MPaG]) in the presence of cobalt acetate, manganese acetate and hydrobromic acid in hydrous acetic acid to obtain a crude isophthalic acid slurry (the concentration of isophthalic acid: 33% by weight; the concentration of water in the hydrous acetic acid that is a dispersing medium: 14% by weight), and the resulting slurry is then introduced into crystallization vessels connected in series to subject the slurry to sequential pressure drop.

Next, the oxidation reaction slurry is cooled to separate the aromatic carboxylic acid crystals therefrom. In the solid-liquid separation step, the crude aromatic carboxylic acid slurry produced in the liquid-phase oxidation reaction is separated into crude aromatic carboxylic acid crystals and an oxidation reaction mother liquor using a solid-liquid separator. The solid-liquid separation is usually carried out under atmospheric pressure and may also be carried out under applied pressure. The temperature in the solid-liquid separation is not particularly limited, and is usually a temperature lower than a boiling point of a solvent as measured under atmospheric pressure, for example, in the range of from 50 to 115° C. The upper limit of the temperature in the separation under applied pressure is 150° C. Examples of the solid-liquid separator include a centrifugal separator, a centrifugal filter, a vacuum filter, and so on.

The oxidation reaction mother liquor separated in the solid-liquid separation step contains the fine crystals containing the aromatic carboxylic acid as a main component, and therefore, is subjected to a cross-flow filtration using a ceramic filter to recover the fine crystals of aromatic carboxylic acid, thereby improving the output level of the aromatic carboxylic acid. In addition, the resulting clear oxidation reaction mother liquor can be directly subjected to a catalyst recovery process using a resin.

A general ceramic filter, which may be a filter utilizing a ceramic porous body is used, for example, for removing suspended matters, bacteria, dusts, etc., in a liquid or gas in a wide range of fields such as water treatment, waste gas treatment, and medical and food fields because it is excellent in physical strength, durability, corrosion resistance or the like.

In the ceramic filter, the ceramic porous body itself may be used as a filtering material; however, in general, in order to enhance both a filtering performance and a fluid penetration rate (i.e., processing capacity), the ceramic porous body is used as a substrate (support), and a filtering membrane of a ceramic material is formed on a surface of the substrate.

For example, whereas the filtering membrane is configured to have an average pore diameter as small as from about 0.01 to about 1.0 μm to ensure a filtering performance, the substrate is configured to have an average pore diameter as large as from about 1 μm to about several hundreds of microns to reduce a flow resistance inside of the substrate and enhance a fluid penetration rate (i.e., processing capacity).

The substrate of the ceramic filter may be formed into various shapes according to the object of the filtration. In general, the substrate may be frequently used in form of a tube having a single flow path or in form of a honeycomb (including a monolith) having a number of flow paths extending in parallel with each other.

The filter in which the filtering membrane is formed on a surface of the tubular or honeycomb-shaped substrate, e.g., on an inner peripheral surface of a flow path therein, is mounted in a housing such that an outer periphery side of the substrate is hermetically isolated from an end surface side of the substrate to which the flow path is opened, by an O-ring, etc., thereby providing a cross-flow filter.

It is preferable that the ceramic filter used in the present invention comprising a ceramic porous body as the substrate (a support member) is in the form of a honeycomb (including a monolith) having a large number of flow paths extending in parallel with each other in the substrate, wherein the filtering membrane composed of a ceramic is formed on an inner peripheral surface of the flow paths. The average pore diameter of the filtering membrane is preferably from 0.1 to 5 μm. As the ceramic filter, a commercially available ceramic filter may be used and the examples include a ceramic membrane filter available from NGK Insulators, Ltd., a ceramic membrane filter available from Pall Corp., and a ceramic membrane filter available from TAMI Industries, France.

Also, a plurality of the ceramic filters may be disposed in parallel with each other according to the amount of throughput.

In the cross-flow type filter, a fluid to be treated such as gas and liquid is fed from one end surface side of the substrate into the flow paths, and then the filtered fluid that penetrates through the filtering membrane disposed on an inner peripheral surface of the flow paths is recovered from the outer peripheral surface side of the substrate. On the other hand, the fluid to be treated which is not filtered can be recovered from the other end surface side of the substrate.

In the above cross-flow filtration, the time of the operation for filtering the fine crystals is from 60 to 1800 seconds and preferably from 120 to 1200 seconds.

When the time of the operation for filtering is 60 seconds or longer, a change-over operation of valves can be prevented from taking place frequently so that a service life of the valves can be maintained. When the time of the operation for filtering is 1800 seconds or shorter, a sufficient average filtering flow rate can be maintained without reducing the filtering flow rate to 0.20 [m$^3$/h] or less at the time of termination in the filtrating. In addition, the filtering performance may be readily restored by a back washing with the filtrate.

The circulating linear velocity of the oxidation reaction mother liquor in the flow path of the ceramic filter upon conducting the operation for filtering the fine crystals is preferably in the range of from 1000 to 10000 [m/h] at an inlet of the flow path. When the circulating linear velocity is 1000 [m/h] or more, it is possible to attain a sufficient effect of removing the fine crystals deposited on a surface of the filtering membrane. On the other hand, when the circulating linear velocity is 10000 [m/h] or less, the differential pressure between an inlet side and an outlet side of the ceramic filter is prevented from increasing excessively, so that a pump for circulating the oxidation reaction mother liquor is not required to have an excessively large capacity (i.e., it is possible to suppress increase in costs for plant investment), and further there occurs no fear of damage to the ceramic filter or O-ring. Meanwhile, when the ceramic filter has a plurality of flow paths or when a plurality of the ceramic filters are used together, the circulating linear velocity in the flow paths of the ceramic filter(s) is defined by an average circulating linear velocity as calculated based on a total sectional area of the whole flow paths.

The filtering linear velocity of the filtrate upon conducting the operation for filtering the fine crystals is preferably in the range of from 0.5 to 3.0 [m/h]. When the filtering linear velocity of the filtrate is 0.5 [m/h] or more, it is possible to attain a sufficient filtering performance. On the other hand, when the filtering linear velocity of the filtrate is 3.0 [m/h] or less, there occurs a less fear of damage to the ceramic filter or O-ring.

The differential pressure between the flow path side and the filtration side upon conducting the operation for filtering the fine crystals is preferably in the range of from 0.05 to 0.5 [MPa].

When the differential pressure is 0.05 [MPa] or more, it is possible to attain a sufficient filtering performance. On the other hand, when the differential pressure is 0.5 [MPa] or less, there occurs a less fear of damage to the ceramic filter or O-ring.

In the above filtration, the fine crystals are gradually deposited on a surface of the filtering membrane so that the filtering flow rate therethrough is lowered. Therefore, while maintaining the flowing circulation operation of the oxidation reaction mother liquor, the filtering operation is changed-over to a back washing with the filtrate. This means an operation of feeding the filtrate from the filtration side to the flow path side, and aims at physically and chemically removing the fine crystals deposited on the surface of the filtering membrane.

In the back washing with the filtrate, the differential pressure between the filtration side and the flow path side is in the range of from 0.10 to 1.0 [MPa] and more preferably from 0.10 to 0.60 [MPa].

When the differential pressure between the filtration side and the flow path side is less than 0.10 [MPa], it may be difficult for the filtrate to uniformly flow through a whole portion of the filtering membrane of the ceramic filter, so that no sufficient washing effect can be obtained. On the other hand, when the differential pressure between the filtration side and the flow path side is more than 1.0 [MPa], it is undesirable since there tends to occur rapid change in pressure so that a possibility of damage to the ceramic filter or seal members therefor is increased.

The feeding linear velocity of the filtrate is in the range of from 1.0 to 20 [m/h], preferably from 1.0 to 15 [m/h], more preferably from 1.0 to 10 [m/h] and still more preferably from 1.0 to 8 [m/h].

When the feeding linear velocity of the filtrate is less than 1.0 [m/h], it may be difficult for the filtrate to uniformly flow through a whole portion of the filtering membrane of the ceramic filter, so that no sufficient washing effect can be obtained. On the other hand, when the feeding linear velocity of the filtrate is more than 20 [m/h], it is undesirable, since there tends to occur rapid change in pressure so that a possibility of damage to the ceramic filter or seal members therefor is increased.

Upon the back washing with the filtrate, it is suitable that the pressure on the flow path side is lowered to produce the differential pressure.

On the flow path side, the oxidation reaction mother liquor is circulated, and in order to regulate the circulating flow rate thereof, there are used control valves disposed on an upstream of a filtering module (on a conduit on the side of feeding the oxidation reaction mother liquor to the filtering module) and on a downstream thereof (on a conduit on the side of feeding the oxidation reaction mother liquor which passes through the flow paths of the ceramic filter back to an oxidation reaction mother liquor vessel from the filtering module). The control valves on the upstream and downstream control not only the circulating flow rate but also a pressure on the flow path side. By using these control valves, it is possible to reduce the pressure on the flow path side. In particular, upon the back washing with the filtrate, the filtrate used in the back washing is merged with the oxidation reaction mother liquor circulated through the flow path, so that the flow rate is increased on the downstream of the filtering module; therefore, it is preferred that an opening degree of the control valve on the downstream is increased, and it is preferred that at the same time an opening degree of the control valve on the upstream is decreased to suppress variation in circulating flow rate on the upstream owing to entrance of the filtrate used for the back washing operation into the flow path. Due to these, it is possible to reduce the pressure in the flow paths as a whole.

In order to remove the fine crystals deposited on the surface of the filtering membrane and solids precipitated inside of the filtering membrane (mainly the aromatic carboxylic acid), it is advantageous that the feeding time of the filtrate upon the back washing is longer. However, in view of a loss of the filtering operation time, it is required that it lies within a certain range. Therefore, the time of the back washing operation with the filtrate is preferably in the range of from 5 to 60 [s] and more preferably from 10 to 40 [s].

The filtrate used in the back washing is mixed with the oxidation reaction mother liquor circulated through the flow path, and therefore, the temperature of the filtrate is preferably equal to or more than the temperature of the oxidation reaction mother liquor. In addition, in order to dissolve the fine crystals deposited on the surface of the filtering membrane and the solids precipitated inside of the filtering membrane (mainly aromatic carboxylic acid) for a short period of time, it is preferred that the temperature of the filtrate is higher than that of the oxidation reaction mother liquor. On the other hand, there is a possibility that the excessively large change in temperature in the ceramic filter causes the damage to the ceramic filter or the O-ring owing to the difference in thermal expansion coefficient between the ceramic filter and the filter housing. Therefore, the upper limit of the temperature of the filtrate used in the back washing is preferably "a temperature higher by 35° C. than that of the oxidation reaction mother liquor" and is more preferably "a temperature higher by 25° C. than that of the oxidation reaction mother liquor".

In the present invention, (I) the operation for filtering the fine crystals; and (II) the back washing operation with the filtrate while maintaining the flowing circulation operation of the oxidation reaction mother liquor are alternately repeated.

As the back washing with the filtrate is repeated, the recovery rate of the filtering performance is gradually reduced, and finally it is not possible to attain a predetermined filtering performance. In the present invention, in such a case, the ceramic filter is cleaned by a back washing with a wash solvent while maintaining the flowing circulation operation of the oxidation reaction mother liquor.

In the present invention, when conducting the back washing operation with the wash solvent while maintaining the flowing circulation operation of the oxidation reaction mother liquor, the wash solvent used therein is required to have a capability of dissolving the fine crystals containing the aromatic carboxylic acid as a main component, and acetic acid, which is used as the solvent in the liquid-phase oxidation reaction, is suitable as the wash solvent. The acetic acid preferably has a water content of from 0.1 to 30% by mass and more preferably from 0.1 to 10% by mass.

When feeding the wash solvent from the filtration side to the flow path side (upon the back washing with the wash solvent), in order to physically and chemically remove the fine crystals deposited on the surface of the filtering membrane, the differential pressure between the filtration side and the flow path side is preferably in the range of from 0.10 to 1.0 [MPa] and more preferably from 0.10 to 0.8 [MPa].

When the differential pressure between the filtration side and the flow path side is 0.10 [MPa] or more, it is possible to allow the wash solvent to uniformly flow through a whole portion of the filtering membrane of the ceramic filter and therefore attain a sufficient washing effect. On the other hand, when the differential pressure between the filtration side and the flow path side is 1.0 [MPa] or less, a rapid variation in pressure does not occur, and there is no possibility of damage to the ceramic filter or seal members therefor.

The feeding linear velocity of the wash solvent is preferably in the range of from 1.0 to 20 [m/h] and more preferably from 1.0 to 15 [m/h].

When the feeding linear velocity of the wash solvent is 1.0 [m/h] or more, it is possible to allow the wash solvent to uniformly flow through a whole portion of the filtering membrane of the ceramic filter and therefore attain a sufficient washing effect. On the other hand, when the feeding linear velocity of the wash solvent is 20 [m/h] or less, there is no possibility of damage to the ceramic filter or seal members therefor by the rapid variation in pressure.

In order to remove the fine crystals deposited on the surface of the filtering membrane and solids precipitated inside of the filtering membrane (mainly the aromatic carboxylic acid), it is advantageous that the feeding time of the wash solvent is longer. However, in view of a loss of the filtering operation time as well as addition of the used wash solvent to the oxidation reaction mother liquor, it is required that the feeding time of the wash solvent lies within a certain range. Therefore, the time of the back washing operation with the wash solvent is preferably in the range of from 5 to 120 [s] and more preferably from 5 to 90 [s].

The wash solvent is mixed with the oxidation reaction mother liquor circulated through the flow path, and therefore, the temperature of the wash solvent is preferably equal to or more than a temperature of the oxidation reaction mother liquor. In addition, in order to dissolve the fine crystals deposited on the surface of the filtering membrane and the solids precipitated inside of the filtering membrane (mainly the aromatic carboxylic acid) for a short period of time, it is preferred that the temperature of the wash solvent is higher than that of the oxidation reaction mother liquor. On the other hand, there is possibility that the excessively large change in temperature in the ceramic filter causes the damage to the ceramic filter or the O-ring owing to the difference in thermal expansion coefficient between the ceramic filter and the filter housing. Therefore, the upper limit of the temperature of the wash solvent is preferably "a temperature higher by 35° C. than that of the oxidation reaction mother liquor" and is more preferably "a temperature higher by 25° C. than that of the oxidation reaction mother liquor".

In the filtering operation method according to the present invention which is conducted by a cross-flow filtration using a ceramic filter comprising: (I) the operation for filtering the fine crystals; (II) the back washing operation with the filtrate while maintaining the flowing circulation operation of the oxidation reaction mother liquor; and (III) the back washing operation with the wash solvent while maintaining the flowing circulation operation of the oxidation reaction mother liquor, the order of the above operations (I), (II) and (III) is not particularly limited, and these operations may be conducted in any order.

However, in the present invention, the method is preferable a periodic operation comprising the operations (I), (II) and (III) in which the operations (I) and (II) are repeated, and when the filtering flow rate is unable to be restored by the operation (II), the operation (III) is carried out.

EXAMPLES

The present invention will be described in more detail below by referring to the following Examples, etc. It should be noted, however, that the present invention is not limited by the following Examples.

In hydrous acetic acid having a water content of 9% by mass, m-xylene was subjected to liquid-phase oxidation reaction by air (reaction temperature: 200 [° C.]; reaction pressure: 1.6 [MPaG]) in the presence of 1000 ppm of cobalt ions, 930 ppm of manganese ions and 950 ppm of bromide ions to thereby obtain a slurry containing a crude isophthalic acid. After conducting post-oxidation reaction, the slurry was introduced into a crystallization step and was subjected to release of pressure and cooled to 100° C. under a normal pressure, and then subjected to solid-liquid separation using a rotary vacuum filter to separate the crude isophthalic acid crystals from the reaction solution, thereby preparing an oxidation reaction mother liquor required for a filtering operation conducted by a cross-flow filtration using a ceramic filter. Meanwhile, the oxidation reaction mother liquor was at 80° C. The oxidation reaction mother liquor was turbid owing to fine crystals, and the content of the fine crystals therein was 0.47% by mass.

A ceramic filter available from NGK Insulators, Ltd., as an element was mounted in a filtering module 7. A ceramic filter 8 was in form of a monolith, a filtering membrane thereof had an average pore diameter of 0.5 μm, and the size was of 30 mmφ×1000 mL. Flow paths 28 had an outer diameter of 4

[mm], and the number of openings thereof was 19. The filtering area of the ceramic filter was 0.2386 [m²], and a total sectional area of the flow paths was 0.0002386 [m²].

Meanwhile, the amount of discarded isophthalic acid in Examples was calculated from the amount of precipitated isophthalic acid in circulating flow rate (0.68 m³/h) of the oxidation reaction mother liquor.

The operation method of cross-flow filtration using a ceramic filter will be explained.

(Operation for Filtering Fine Crystals)

Figure 2:
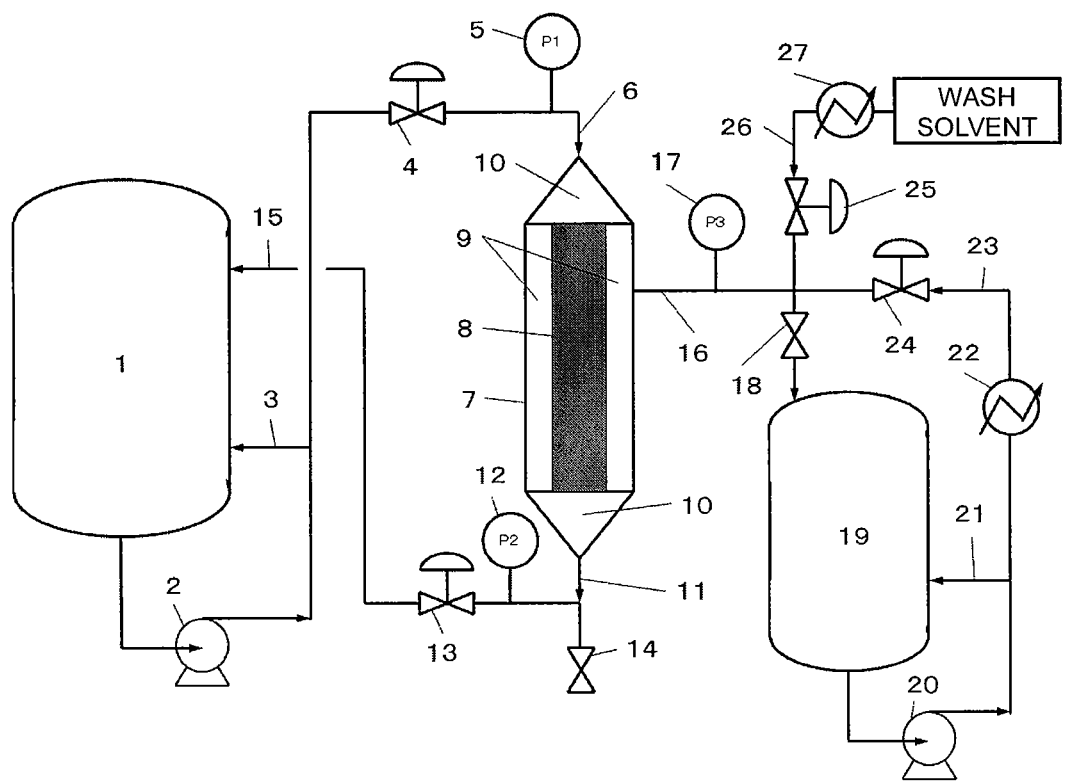
FIG. 2 is a pipeline diagram showing another embodiment of the present invention.
Figure 3:
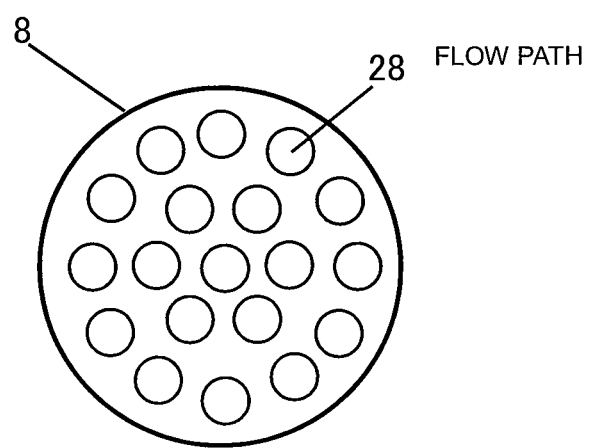
FIG. 3 is a sectional view of a ceramic filter shown in FIG. 1 or FIG. 2.

In FIG. 1 to FIG. 3, the above-mentioned oxidation reaction mother liquor is stored in an oxidation reaction mother liquor vessel 1. The oxidation reaction mother liquor is fed to an upper substrate end surface side 10 of a filtering module 7 through a circulation inlet conduit 6 using a pump 2. At this time, the flow rate thereof is regulated by a control valve 4. The oxidation reaction mother liquor fed to the filtering module 7 passes through flow paths 28 in a ceramic filter 8, and then passes through a lower substrate end surface side 10 and a circulation outlet conduit 11, and is fed back to the oxidation reaction mother liquor vessel 1. At this time, a flow rate thereof is regulated by a control valve 13.

A series of the above flows is called an oxidation reaction mother liquor circulation line. In the mother liquor circulation line, by controlling the control valves 4 and 13, the circulating flow rate of the mother liquor is regulated. Further, a pressure on the side of the flow path 28 of the ceramic filter 8, namely, a pressure on an upstream side of the filter (primary pressure), is controlled. The pressure is determined by pressure gauges 5 and 12.

The filtering operation of the oxidation reaction mother liquor is conducted by establishing the mother liquor circulation line and then opening a valve 18 (while closing control valves 24 and 25). At this time, the oxidation reaction mother liquor is filtered through the ceramic filter 8, and thereby a clear oxidation reaction mother liquor from which the fine crystals are removed is discharged to a filtration side 9, and then passes through a filtrate outlet conduit 16 and is stored in a filtrate vessel 19. A pressure on a downstream side of the filter (secondary pressure) during the filtering operation is determined by a pressure gauge 17.

The filtering flow rate is determined from a filtering differential pressure between the primary pressure and the secondary pressure, properties of the fluid to be filtered (such as viscosity) and a filtering performance of the ceramic filter 8 (such as filtering area, average pore diameter and degree of clogging).

The filtering differential pressure $\Delta P$ [MPa] is calculated according to the following formula:

$$\Delta P = (P1+P2)/2 - P3$$

wherein a pressure at the pressure gauge 5 is P1 [MPaG]; a pressure at the pressure gauge 12 is P2 [MPaG]; and a pressure at the pressure gauge 17 is P3 [MPaG].

(Back Washing Operation with Filtrate)

In FIG. 1 to FIG. 3, when the filtering flow rate upon the operation for filtering the fine crystals is lowered, a back washing operation with the filtrate is conducted. First, the valve 18 is closed (while keeping the control valves 24 and 25 in a closed state) to terminate the operation for filtering (but while continuing circulation of the mother liquor). Next, the control valve 24 is opened while controlling, and the filtrate in the filtrate vessel 19 is fed to the filtration side 9 of the filtering module 7 through a filtrate back washing conduit 23 using a pump 20. At this time, if required, a temperature of the filtrate is controlled by a heat exchanger 22. The pressure on the filtration side 9 is made to be higher than the pressure on the flow path side 28 (back washing differential pressure), so that the filtrate passes from the filtration side 9 to the flow path side 28 to conduct a back washing. The back washing differential pressure is defined by $-\Delta P$.

Meanwhile, the control valves 4 and 13 may be appropriately controlled upon the back washing such that the pressure on the flow path side 28 is lowered to adjust the back washing differential pressure.

(Back Washing Operation with Wash Solvent)

In FIG. 2, when the back washing operation with the filtrate fails to fully restore the filtering flow rate, a back washing operation with a wash solvent is conducted. First, the valve 18 and the control valve 24 are closed (while continuing circulation of the mother liquor). Next, the control valve 25 is opened while controlling to feed the wash solvent to the filtration side 9 of the filtering module 7 through a wash solvent back washing conduit 26. At this time, if required, a temperature of the wash solvent is controlled by a heat exchanger 27. The pressure on the filtration side 9 is made to be higher than the pressure on the flow path side 28, so that the wash solvent passes from the filtration side 9 to the flow path 28 side to conduct the back washing. The passing wash solvent is mixed with the oxidation reaction mother liquor circulated therethrough.

Meanwhile, the control valves 4 and 13 may be appropriately controlled upon the back washing such that the pressure on the flow path 28 side is lowered to adjust the back washing differential pressure.

Further, an average filtering flow rate $X_1$ upon conducting the operation for filtering the fine crystals; a circulating linear velocity $LV_1$ of the oxidation reaction mother liquor in the flow path of the ceramic filter; and a filtering linear velocity $LV_2$ of the filtrate are determined according to the following formulae. Meanwhile, $LV_1$ is determined as an average circulating linear velocity.

Circulating flow rate at an inlet of filtering module 7: F [m³/h]
Time of the operation for filtering fine crystals: $T_1$ [s]
Filtering flow rate upon initiation of the operation for filtering fine crystals: $X_s$ [m³/h]
Filtering flow rate upon termination of the operation for filtering fine crystals: $X_t$ [m³/h]
Average filtering flow rate upon conducting the operation for filtering fine crystals:

$$X_1 [m^3/h] = (X_s + X_t)/2$$

Circulating linear velocity of oxidation reaction mother liquor in flow path of ceramic filter:

$$LV_1 [m/h] = F/0.0002386$$

Filtering linear velocity of filtrate:

$$LV_2 [m/h] = X_s/0.2386$$

In addition, an average filtering flow rate $V_3$ during one cycle of the operation for filtering the fine crystals and the back washing operation with the filtrate; and a feeding linear velocity $LV_3$ of the filtrate upon the back washing operation are determined according to the following.

Total amount of filtrate in the operation for filtering fine crystals:

$$V_1 [m^3] = T_1 \times X_1/3600$$

Time of back washing operation with filtrate: $T_2$ [s]
Back washing flow rate upon back washing operation with filtrate: $X_2$ [M³/h]
Total amount of back washing fluid upon back washing operation with filtrate:

$$V_2 [m^3] = T_2 \times X_2/3600$$

Average filtering flow rate during one cycle of the operation for filtering fine crystals and back washing operation with filtrate:

$$V_3[m^3/h]=(V_1-V_2)/(T_1+T_2)\times 3600$$

Feeding linear velocity upon back washing operation with filtrate:

$$LV_3[m/h]=X_2/0.2386$$

As the used amount of the filtrate upon the back washing operation with the filtrate increases, a net amount of the obtained filtrate becomes smaller, and the average filtering flow rate $V_3$ during one cycle of the operation for filtering the fine crystals and the back washing operation with the filtrate is reduced.

Example 1

Operation for Filtering Fine Crystals

The above-mentioned oxidation reaction mother liquor (80° C.) was fed to the filtering module 7 at a circulation inlet flow rate of 0.68 [m³/h] (P1=0.10 [MPaG]) (down flow) to initiate a cross-flow filtering. The filtering flow rate $X_s$ upon initiation of the operation for filtering the fine crystals was 0.32 [m³/h] (P3=0.00 [MPaG]), and the circulation outlet flow rate was 0.36 [m³/h] (P2=0.09 [MPaG]). The differential pressure ΔP between the flow path side and the filtration side was 0.10 [MPa]. Also, the circulating linear velocity in the flow paths and the filtering linear velocity of the filtrate were 2848 (m/h) and 1.34 (m/h), respectively.
(Back Washing Operation with Filtrate)

When continuing the operation for filtering, the filtering flow rate was decreased down to 0.20 [m³/h] after the elapse of 500 seconds (the filtering flow rate $X_t$ upon termination of the operation for filtering the fine crystals was 0.20 [m³/h]). Therefore, while continuing circulation of the oxidation reaction mother liquor, the back washing operation with the filtrate was conducted for 15 seconds (feeding linear velocity: 2.85 [m/h]; temperature of filtrate: 80° C.). At this time, the respective pressures were P1=0.14 [MPaG], P2=0.10 [MPaG] and P3=0.31 [MPaG], and the differential pressure −ΔP between the filtration side and the flow path side was 0.19 [MPa].

The back washing operation with the filtrate was terminated and changed back to the operation for filtering. At this time, the filtering flow rate (immediately after the back washing with the filtrate in the 1st cycle=$X_s$ in the 2nd cycle) was 0.32 [m³/h], and the average filtering flow rate $V_3$ in the 1st cycle of the operation for filtering the fine crystals and the back washing operation with the filtrate was 0.233 [m³/h]. Also, the filtering flow rate immediately after the back washing with the filtrate in the 2nd cycle was 0.32 [m³/h], and the average filtering flow rate $V_3$ in the 2nd cycle was 0.233 [m³/h].

The filtering flow rates immediately after the back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 15 seconds) were alternately and continuously repeated. As a result, the ceramic filter was able to maintain its filtering performance for filtering the fine crystals until the elapse of 6 hours when the filtering flow rate immediately after the back washing with the filtrate was unable to be restored to 0.25 [m³/h] or more. The results are shown in Table 1.

Example 2

The operation for filtering and the back washing operation with the filtrate were alternately and continuously repeated in the same manner as in Example 1 except that the back washing operation with the filtrate was conducted at a feeding linear velocity of 5.70 [m/h] for 10 seconds as the time of the back washing operation. Upon conducting the back washing operation with the filtrate, the respective pressures were P1=0.16 [MPaG], P2=0.11 [MPaG] and P3=0.53 [MPaG], and the differential pressure −ΔP upon the back washing between the filtration side and the flow path side was 0.40 [MPa].

The back washing operation with the filtrate was terminated and changed back to the operation for filtering. At this time, the filtering flow rate (immediately after the back washing with the filtrate in the 1st cycle) was 0.32 [m³/h], and the average filtering flow rate $V_3$ in the 1st cycle was 0.228 [m³/h]. Also, the filtering flow rate immediately after the back washing operation with the filtrate in the 2nd cycle was 0.32 [m³/h], and the average filtering flow rate $V_3$ in the 2nd cycle was 0.228 [m³/h].

The filtering flow rates immediately after the back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 10 seconds) were alternately and continuously repeated. As a result, the ceramic filter was able to maintain its performance for filtering the fine crystals until the elapse of 8 hours when the filtering flow rate immediately after the back washing with the filtrate was unable to be restored to 0.25 [m³/h] or more. The results are shown in Table 1.

Example 3

The operation for filtering and the back washing operation with the filtrate were alternately and continuously repeated in the same manner as in Example 1 except that the back washing operation with the filtrate was conducted at a feeding linear velocity of 1.42 [m/h] with a filtrate temperature of 90° C. for 30 seconds as the time of the back washing operation. Upon conducting the back washing operation with the filtrate, the respective pressures were P1=0.12 [MPaG], P2=0.10 [MPaG] and P3=0.21 [MPaG], and the differential pressure −ΔP upon the back washing between the filtration side and the flow path side was 0.10 [MPa].

The back washing operation with the filtrate was terminated and changed back to the operation for filtering. At this time, the filtering flow rate (immediately after the back washing with the filtrate in the 1st cycle) was 0.32 [m³/h], and the average filtering flow rate $V_3$ in the 1st cycle was 0.226 [m³/h]. Also, the filtering flow rate immediately after the back washing with the filtrate in the 2nd cycle was 0.32 [m³/h], and the average filtering flow rate $V_3$ in the 2nd cycle was 0.226 [m³/h].

The filtering flow rates immediately after the back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 30 seconds) were alternately and continuously repeated. As a result, the ceramic filter was able to maintain its performance for filtering the fine crystals until the elapse of 6 hours when the filtering flow rate immediately after the back washing with the filtrate was unable to be restored up to 0.25 [m³/h] or more. The results are shown in Table 1.

Example 4

The operation for filtering and the back washing operation with the filtrate were alternately and continuously repeated in the same manner as in Example 1 except that upon the back washing operation with the filtrate, the opening degrees of the upstream control valve 4 and the downstream control valve 13 for reducing the pressure on the flow path side were not controlled. Upon conducting the back washing with the filtrate, the respective pressures were P1=0.36 [MPaG], P2=0.31 [MPaG] and P3=0.51 [MPaG], and the differential pressure $-\Delta P$ upon the back washing between the filtration side and the flow path side was 0.18 [MPa].

The back washing operation with the filtrate was terminated and changed back to the operation for filtering. At this time, the filtering flow rate (immediately after the back washing with the filtrate in the 1st cycle) was restored to merely 0.31 [m³/h], and the average filtering flow rate $V_3$ in the 1st cycle was 0.233 [m³/h].

The filtering flow rate immediately after the back washing operation with the filtrate in the 2nd cycle was restored to 0.31 [m³/h], and the average filtering flow rate $V_3$ in the 2nd cycle was 0.228 [m³/h].

The filtering flow rates immediately after the back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 15 seconds) were alternately and continuously repeated. As a result, the ceramic filter was able to maintain its performance for filtering the fine crystals until the elapse of 3 hours when the filtering flow rate immediately after the back washing with the filtrate was unable to be restored to 0.25 [m³/h] or more. The results are shown in Table 1.

Thus, since the opening degrees of the upstream control valve 4 and the downstream control valve 13 for reducing the pressure on the flow path side were not controlled, the filtrate flowing into the flow path upon the back washing with the filtrate caused reduction in the flow rate of the oxidation reaction mother liquor entering into the ceramic filter from the upper substrate end surface side, thereby deteriorating the effect of physically removing the fine crystals deposited on the surface of the filtering membrane. The results are also shown in Table 1.

Comparative Example 1

The operation for filtering and the back washing operation with the filtrate were alternately and continuously repeated in the same manner as in Example 1 except that the back washing operation with the filtrate was conducted for 70 seconds. Upon conducting the back washing operation with the filtrate, the respective pressures were P1=0.14 [MPaG], P2=0.10 [MPaG] and P3=0.31 [MPaG], and the differential pressure $-\Delta P$ upon the back washing between the filtration side and the flow path side was 0.19 [MPa].

The back washing operation with the filtrate was terminated and changed back to the operation for filtering. At this time, the filtering flow rate (immediately after the back washing with the filtrate in the 1st cycle) was 0.32 [m³/h], and the average filtering flow rate $V_3$ in the 1st cycle was 0.145 [m³/h]. Also, the filtering flow rate immediately after the back washing operation with the filtrate in the 2nd cycle was 0.32 [m³/h], and the average filtering flow rate $V_3$ in the 2nd cycle was 0.145 [m³/h].

The filtering flow rates immediately after the cycle back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 70 seconds) were alternately and continuously repeated. As a result, the ceramic filter was able to maintain its performance for filtering the fine crystals until the elapse of 6 hours when the filtering flow rate as measured immediately after the back washing with the filtrate was unable to be restored to 0.25 [m³/h] or more. The results are shown in Table 1.

However, since the back washing operation with the filtrate was conducted for a prolonged time, the average filtering flow rate $V_3$ was 0.145 [m³/h]. The low average filtering flow rate resulted in increased number of filter elements required, thereby causing increase in costs. The results are also shown in Table 1.

Comparative Example 2

The operation for filtering and the back washing operation with the filtrate were alternately repeated in the same manner as in Example 1 except that the back washing operation with the filtrate was conducted at a feeding linear velocity of 0.84 [m/h]. Upon conducting the back washing operation with the filtrate, the respective pressures were P1=0.11 [MPaG], P2=0.09 [MPaG] and P3=0.15 [MPaG], and the differential pressure $-\Delta P$ upon the back washing between the filtration side and the flow path side was 0.05 [MPa].

The back washing operation with the filtrate was terminated and changed back to the operation for filtering, but the filtering flow rate upon initiation of the operation for filtering the fine crystals was restored to only 0.25 [m³/h]. Moreover the average filtering flow rate $V_3$ in the 1st cycle of the operation for filtering the fine crystals and the back washing operation with the filtrate was 0.247 [m³/h].

Next, the operation for filtering of the 2nd cycle was initiated. However, after the elapse of 60 s, the filtering flow rate was decreased down to 0.20 [m³/h] so that the time of the operation for filtering the fine crystals which was set to $T_1$=500 s was unable to be maintained. The results are shown in Table 1.

Comparative Example 3

The operation for filtering and the back washing operation with the filtrate were alternately repeated in the same manner as in Example 1 except that the back washing operation with the filtrate was conducted at a filtrate temperature of 70° C. Upon conducting the back washing operation with the filtrate, the respective pressures were P1=0.14 [MPaG], P2=0.10 [MPaG] and P3=0.34 [MPaG], and the differential pressure $-\Delta P$ upon the back washing between the filtration side and the flow path side was 0.22 [MPa].

The back washing operation with the filtrate was terminated and changed back to the operation for filtering, but the filtering flow rate upon initiation of the operation for filtering the fine crystals was restored to only 0.24 [m³/h], and the average filtering flow rate $V_3$ in the 1st cycle was 0.233 [m³/h].

Next, the operation for filtering of the 2nd cycle was initiated. However, after the elapse of 60 seconds, the filtering flow rate was decreased down to 0.20 [m³/h] so that the setting in which the time of the operation for filtering the fine crystals $T_1$ was 500 seconds was unable to be maintained. The results are shown in Table 1.

The reason therefor was that since the temperature of the filtrate upon the back washing operation with the filtrate was as low as 70° C., it was not possible to clean the ceramic filter to a sufficient extent.

Comparative Example 4

The operation for filtering and the back washing-operation with the filtrate were alternately and continuously repeated in the same manner as in Example 1 except that the back washing operation with the filtrate was conducted at a feeding linear velocity of 0.84 [m/h] with a filtrate temperature of 90° C. the time of the back washing operation of 300 seconds. Upon conducting the back washing operation with the filtrate, the respective pressures were P1=0.11 [MPaG], P2=0.09 [MPaG] and P3=0.15 [MPaG], and the differential pressure −ΔP upon the back washing between the filtration side and the flow path side was 0.05 [MPa].

The back washing operation with the filtrate was terminated and changed back to the operation for filtering. At this time, the filtering flow rate (immediately after the back washing with the filtrate in the 1st cycle) was 0.32 [m³/h], and the average filtering flow rate $V_3$ in the 1st cycle was 0.088 [m³/h]. Also, the filtering flow rate immediately after the back washing with the filtrate in the 2nd cycle was 0.32 [m³/h], and the average filtering flow rate $V_3$ in the 2nd cycle was 0.088 [m³/h].

The filtering flow rates immediately after the back washing with the filtrate and the average filtering flow rates $V_3$ in the 3rd to 5th cycles were respectively the same as those in the 2nd cycle.

Further, the operation for filtering (for 500 seconds) and the back washing operation with the filtrate (for 300 seconds) were alternately and continuously repeated. As a result, the ceramic filter was able to maintain its performance for filtering the fine crystals until the elapse of 1.5 h when the filtering flow rate as measured immediately after the back washing operation with the filtrate was unable to be restored up to 0.25 [m³/h] or more.

However, even under the conditions in this Comparative Example, the average filtering flow rate $V_3$ was 0.088 [m³/h]. The average filtering flow rate was low, which resulted in increase in number of filter elements required, thereby causing increase in costs. The results are shown in Table 1.

TABLE 1

|  | Examples | | | |
| --- | --- | --- | --- | --- |
|  | 1 | 2 | 3 | 4 |
| (Operation conditions) | | | | |
| Time of operation for filtering fine crystals $T_1$ [s] | 500 | 500 | 500 | 500 |
| Time of back washing operation with filtrate $T_2$ [s] | 15 | 10 | 30 | 15 |
| Feeding linear velocity of filtrate upon back washing operation [m/h] | 2.85 | 5.70 | 1.42 | 2.85 |
| Back washing flow rate of filtrate $X_2$ [m³/h] | 0.68 | 1.36 | 0.34 | 0.68 |
| Filtrate temperature [° C.] | 80 | 80 | 90 | 80 |
| Differential pressure upon back washing -ΔP [MPa] | 0.19 | 0.40 | 0.10 | 0.18 |
| Other operations | — | — | — | *1 |
| (Results of operations) | | | | |
| Filtering flow rate immediately after back washing of 1st cycle with filtrate [m³/h] | 0.32 | 0.32 | 0.32 | 0.31 |
| Average filtering flow rate $V_3$ in 1st cycle [m³/h] | 0.233 | 0.228 | 0.226 | 0.233 |
| Filtering flow rate immediately after back washing of 2nd cycle with filtrate [m³/h] | 0.32 | 0.32 | 0.32 | 0.31 |
| Average filtering flow rate $V_3$ in 2nd cycle [m³/h] | 0.233 | 0.228 | 0.226 | 0.228 |
| Results of operations in $3^{rd}$ to 5th cycles | *2 | *2 | *2 | *2 |
| Time elapsed until performance for filtering fine crystals became unable to be maintained [hrs] | 6 | 8 | 6 | 3 |

|  | Comparative Examples | | | |
| --- | --- | --- | --- | --- |
|  | 1 | 2 | 3 | 4 |
| (Operation conditions) | | | | |
| Time of operation for filtering fine crystals $T_1$ [s] | 500 | 500 | 500 | 500 |
| Time of back washing operation with filtrate $T_2$ [s] | 70 | 15 | 15 | 300 |
| Feeding linear velocity of filtrate upon back washing operation [m/h] | 2.85 | 0.84 | 2.85 | 0.84 |
| Back washing flow rate of filtrate $X_2$ [m³/h] | 0.68 | 0.20 | 0.68 | 0.20 |
| Filtrate temperature [° C.] | 80 | 80 | 70 | 90 |
| Differential pressure upon back washing -ΔP [MPa] | 0.19 | 0.05 | 0.22 | 0.05 |

TABLE 1-continued (Results of operations)

| | | | | |
|---|---|---|---|---|
| Filtering flow rate immediately after back washing of 1st cycle with filtrate [m³/h] | 0.32 | 0.25 | 0.24 | 0.32 |
| Average filtering flow rate $V_3$ in 1st cycle [m³/h] | 0.145 | 0.247 | 0.233 | 0.088 |
| Filtering flow rate immediately after back washing of 2nd cycle with filtrate [m³/h] | 0.32 | — | — | 0.32 |
| Average filtering flow rate $V_3$ in 2nd cycle [m³/h] | 0.145 | — | — | 0.088 |
| Results of operations in 3rd to 5th cycles | *2 | — | — | *2 |
| Time elapsed until performance for filtering fine crystals became unable to be maintained [hrs] | 6 | — | — | 1.5 |
| Remarks | | *3 | *3 | |

Note:
*1: Different valve operations;
*2: Same as those at 2nd cycle;
*3: $T_1$ was unable to be maintained at 2nd cycle

Example 5

Operation for Filtering Fine Crystals

The above-mentioned oxidation reaction mother liquor (80° C.) was fed to the filtering module 7 at a circulation inlet flow rate of 0.68 [m³/h] (P1=0.10 [MPaG]) (down flow) to initiate a cross-flow filtration. At this time, the filtering flow rate was 0.32 [m³/h] (P3=0.00 [MPaG]), and the circulation outlet flow rate was 0.36 [m³/h] (P2=0.09 [MPaG]). The differential pressure ΔP between the flow path side and the filtration side was 0.10 [MPa]. Also, the circulating linear velocity in the flow paths and the filtering linear velocity of the filtrate were 2848 (m/h) and 1.34 (m/h), respectively.
(Back Washing Operation with Filtrate)

When continuing the operation for filtering, the filtering flow rate was decreased down to 0.20 [m³/h] after the elapse of 500 seconds, and therefore, while continuing circulation of the oxidation reaction mother liquor, the back washing operation with the filtrate was conducted for 15 seconds (back washing flow rate: 0.68 [m³/h]). At this time, the respective pressures were P1=0.14 [MPaG], P2=0.10 [MPaG] and P3=0.31 [MPaG], and the differential pressure −ΔP between the filtration side and the flow path side was 0.19 [MPa].

The back washing operation with the filtrate was terminated and changed back to the operation for filtering. At this time, the filtering flow rate was 0.32 [m³/h].
(Back Washing Operation with Wash Solvent)

The operation for filtering (for 500 seconds) and the back washing operation with the filtrate (for 15 seconds) were alternately and continuously repeated and after the elapse of 6 hours, the filtering flow rate was unable to be restored to 0.24 [m³/h] or more even immediately after the back washing operation with the filtrate. Therefore, while continuing circulation of the oxidation reaction mother liquor, the back washing operation with acetic acid (water content: 7.7% by mass; 85° C.) as a wash solvent was conducted for 15 seconds (back washing flow rate: 0.68 [m³/h]). The feeding linear velocity of the acetic acid was 2.85 [m/h]. At this time, the respective pressures were P1=0.13 [MPaG], P2=0.10 [MPaG] and P3=0.30 [MPaG], and the differential pressure −ΔP between the filtration side and the flow path side was 0.19 [MPa].

The back washing operation with the acetic acid was terminated and changed back to the operation for filtering. At this time, the filtering flow rate was restored to 0.32 [m³/h]. Next, the operation for filtering and the back washing operation with the filtrate were alternately repeated again. The period was 6 hours until the filtering flow rate became unable to be restored to 0.24 [m³/h] or more immediately after the back washing operation with the filtrate, thereby conducting the next back washing with the wash solvent. That is, while alternately repeating the operation for filtering and the back washing operation with the filtrate, the back washing operation with the wash solvent was conducted in every six-hour period, so that the ceramic filter was able to well maintain its filtering performance. The results are shown in Table 2.

Example 6

The operation for filtering (for 500 s) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing with the filtrate, and therefore, while continuing circulation of the oxidation reaction mother liquor, the back washing operation with acetic acid (water content: 7.7% by mass; 85° C.) was conducted for 15 seconds (back washing flow rate: 1.36 [m³/h]). The feeding linear velocity of the acetic acid was 5.70 [m/h]. At this time, the respective pressures were P1=0.15 [MPaG], P2=0.11 [MPaG] and P3=0.51 [MPaG], and the differential pressure −ΔP between the filtration side and the flow path side was 0.38 [MPa].

The back washing operation with the acetic acid was terminated and changed back to the operation for filtering. At this time, the filtering flow rate was restored to 0.32 [m³/h].

The period until conducting the next back washing with the wash solvent was 6 hours. That is, while alternately repeating the operation for filtering and the back washing operation with the filtrate, the back washing operation with the wash solvent was conducted in every six-hour period, so that the ceramic filter was able to well maintain its filtering performance. The results are shown in Table 2.

Example 7

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, while continuing circulation of the oxidation reaction mother liquor, the back washing operation with acetic acid (water content: 7.7% by mass; 85° C.) was conducted for 10 seconds (back washing flow rate: 2.04 [m³/h]). The feeding linear velocity of the acetic acid was 8.54 [m/h]. At this time, the respective pressures were P1=0.18 [MPaG], P2=0.12 [MPaG] and P3=0.69 [MPaG], and the differential pressure −ΔP between the filtration side and the flow path side was 0.54 [MPa].

The back washing operation with the acetic acid was terminated and changed back to the operation for filtering. At this time, the filtering flow rate was restored to 0.32 [m³/h]. The period until conducting the next back washing operation with the wash solvent was 6 hours. That is, while alternately repeating the operation for filtering and the back washing operation with the filtrate, the back washing with the wash solvent was conducted in every six-hour period, so that the ceramic filter was able to well maintain its filtering performance. The results are shown in Table 2.

Example 8

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, while continuing circulation of the oxidation reaction mother liquor, the back washing operation with acetic acid (water content: 7.7% by mass; 85° C.) was conducted for 60 seconds (back washing flow rate: 0.34 [m³/h]). The feeding linear velocity of the acetic acid was 1.42 [m/h]. At this time, the respective pressures were P1=0.11 [MPaG], P2=0.09 [MPaG] and P3=0.22 [MPaG], and the differential pressure −ΔP between the filtration side and the flow path side was 0.12 [MPa].

The back washing operation with the acetic acid was terminated and changed back to the operation for filtering. At this time, the filtering flow rate was restored up to 0.32 [m³/h]. The period until conducting the next back washing operation with the wash solvent was 4 hours. Furthermore, the period until conducting the further next back washing operation with the wash solvent was also 4 hours. That is, while alternately repeating the operation for filtering and the back washing operation with the filtrate, the back washing operation with the wash solvent was conducted in every four-hour period, so that the ceramic filter was able to well maintain its filtering performance. The results are shown in Table 2.

Example 9

The operation for filtering (for 120 seconds) and the back washing operation with the filtrate (for 15 seconds) were alternately and continuously repeated (for 8 hours) in the same manner as in Example 5. As a result, the filtering flow rate was unable to be restored to 0.24 [m³/h] or more immediately after the back washing operation with the filtrate, and therefore, while continuing circulation of the oxidation reaction mother liquor, the back washing operation with acetic acid (water content: 7.7% by mass; 85° C.) was conducted for 15 seconds (back washing flow rate: 0.68 [m³/h]). The feeding linear velocity of the acetic acid was 2.85 [m/h]. At this time, the respective pressures were P1=0.13 [MPaG], P2=0.10 [MPaG] and P3=0.30 [MPaG], and the differential pressure −ΔP between the filtration side and the flow path side was 0.19 [MPa].

The back washing operation with the acetic acid was terminated and changed back to the operation for filtering. At this time, the filtering flow rate was restored up to 0.32 [m³/h]. The period until conducting the next back washing operation with the wash solvent was 8 hours. That is, while alternately repeating the operation for filtering and the back washing operation with the filtrate, the back washing operation with the wash solvent was conducted in every eight-hour period, so that the ceramic filter was able to well maintain its filtering performance. The results are shown in Table 2.

Example 10

The operation for filtering (for 900 seconds) and the back washing operation with the filtrate (for 15 seconds) were alternately and continuously repeated (for 3 hours) in the same manner as in Example 5. As a result, the filtering flow rate was unable to be restored to 0.24 [m³/h] or more immediately after the back washing with the filtrate, and therefore, while continuing circulation of the oxidation reaction mother liquor, the back washing operation with acetic acid (water content: 7.7% by mass; 85° C.) was conducted for 15 seconds (back washing flow rate: 0.68 [m³/h]). The feeding linear velocity of the acetic acid was 2.85 [m/h]. At this time, the respective pressures were P1=0.13 [MPaG], P2=0.10 [MPaG] and P3=0.30 [MPaG], and the differential pressure −ΔP between the filtration side and the flow path side was 0.19 [MPa].

The back washing operation with the acetic acid was terminated and changed back to the operation for filtering. At this time, the filtering flow rate was restored to 0.32 [m³/h]. The period until conducting the next back washing operation with the wash solvent was 3 hours. That is, while alternately repeating the operation for filtering and the back washing operation with the filtrate, the back washing operation with the wash solvent was conducted in every three-hour period, so that the ceramic filter was able to well maintain its filtering performance. The results are shown in Table 2.

Comparative Example 5

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, the circulation of the oxidation reaction mother liquor was terminated (i.e., the control valves 4 and 13 were closed, and then a drain valve 14 was opened), and then the back washing operation with acetic acid (water content: 7.7% by mass; 85° C.) was conducted for 180 seconds (back washing flow rate: 0.68 [m³/h]). The feeding linear velocity of the acetic acid was 2.85 [m/h]. At this time, the respective pressures were P1=0.00 [MPaG], P2=0.00 [MPaG] and P3=0.19 [MPaG], and the differential pressure −ΔP between the filtration side and the flow path side was 0.19 [MPa].

The back washing operation discharging the wash solvent (acetic acid) out of the system was terminated and changed back to the operation for filtering. At this time, although the filtering flow rate was restored up to 0.32 [m³/h], the used amount of the acetic acid therein was 0.0340 [m³], i.e., as large as 12 times that used in Example 5. Further, 0.37% by weight of isophthalic acid contained in the oxidation reaction mother liquor was discharged as a waste out of the system. Meanwhile, the period until conducting the next back washing operation with the wash solvent was 6 hours. The results are shown in Table 2.

Comparative Example 6

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, the circulation of the oxidation reaction mother liquor was terminated (i.e., the control valves 4 and 13 were closed, and then the drain valve 14 was opened), and the back washing with acetic acid (water content: 7.7% by mass; 85° C.) was conducted for 15 seconds (back washing flow rate: 0.68 [m³/h]). The feeding linear velocity of the acetic acid was 2.85 [m/h]. At this time, the respective pressures were P1=0.00 [MPaG], P2=0.00 [MPaG] and P3=0.19 [MPaG], and the differential pressure −ΔP between the filtration side and the flow path side was 0.19 [MPa].

The back washing operation discharging the wash solvent (acetic acid) out of the system was terminated and changed back to the operation for filtering. Although the amount of the acetic acid used therein was 0.0028 [m³] same as that used in Example 5, it was difficult to remove the fine crystals deposited on the filtering surface on the flow path side owing to no circulation of the mother liquor, so that the filtering flow rate was restored to only 0.26 [m³/h]. For this reason, the period until conducting the 2nd or subsequent back washing operation with the wash solvent was extremely shortened to 30 min. That is, the period of the operation capable of maintaining a good filtering performance of the ceramic filter became extremely short. The results are shown in Table 2.

Further, 6.67% by weight of isophthalic acid contained in the oxidation reaction mother liquor were discharged as a waste out of the system. The results are also shown in Table 2.

Example 11

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, while continuing the circulation of the oxidation reaction mother liquor, the back washing operation with acetic acid (water content: 7.7% by mass; 85° C.) as a wash solvent was conducted for 180 seconds (back washing flow rate: 0.68 [m³/h]). The feeding linear velocity of the acetic acid was 2.85 [m/h]. At this time, the respective pressures were P1=0.13 [MPaG], P2=0.10 [MPaG] and P3=0.30 [MPaG], and the differential pressure −ΔP between the filtration side and the flow path side was 0.19 [MPa].

The back washing operation with the hydrous acetic acid was terminated and changed back to the operation for filtering. At this time, although the filtering flow rate was restored to 0.32 [m³/h], the amount of the acetic acid used therein was 0.034 [m³], i.e., as large as 12 times that used in Example 5. The period until conducting the next back washing with the wash solvent was 6 hours. The results are shown in Table 2.

Example 12

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, while continuing the circulation of the oxidation reaction mother liquor, the back washing operation with acetic acid (water content: 7.7% by mass; 85° C.) was conducted for 15 seconds (back washing flow rate: 0.14 [m³/h]). The feeding linear velocity of the acetic acid was 0.59 [m/h]. At this time, the respective pressures were P1=0.10 [MPaG], P2=0.09 [MPaG] and P3=0.18 [MPaG], and the differential pressure −ΔP between the filtration side and the flow path side was 0.09 [MPa].

The back washing operation with the acetic acid was terminated and changed back to the operation for filtering. The used amount of the acetic acid therein was as small as 0.00058 [m³] (i.e., 0.21 time that used in Example 5), and the filtering flow rate was restored to only 0.27 [m³/h]. For this reason, the period until conducting the 2nd or subsequent back washing operation with the wash solvent was extremely shortened to 1 hour. That is, the period of the operation capable of maintaining a good filtering performance of the ceramic filter became extremely short. The results are shown in Table 2.

Example 13

The operation for filtering (for 500 seconds) and the back washing operation with the filtrate (for 15 seconds) were alternately and continuously repeated (for 6 hours) in the same manner as in Example 5. As a result, the filtering flow rate was unable to be restored to 0.24 [m³/h] or more immediately after the back washing operation with the filtrate, and therefore, while continuing the circulation of the oxidation reaction mother liquor, the back washing operation with acetic acid (water content: 7.7% by mass; 85° C.) as a wash solvent was conducted for 15 seconds (back washing flow rate: 5.10 [m³/h]). The feeding linear velocity of the acetic acid was 21.4 [m/h]. At this time, the respective pressures were P1=0.40 [MPaG], P2=0.31 [MPaG] and P3=1.41 [MPaG], and the differential pressure −ΔP between the filtration side and the flow path side was 1.06 [MPa].

The back washing operation with the acetic acid was terminated and changed back to the operation for filtering. At this time, although the filtering flow rate was restored to 0.32 [m³/h], the used amount of the acetic acid therein was 0.0213 [m³], i.e., as large as 7.6 times that used in Example 5. The period until conducting the next back washing with the wash solvent was 6 hours. The results are shown in Table 2.

TABLE 2

| | Examples | | | | | |
|---|---|---|---|---|---|---|
| | 5 | 6 | 7 | 8 | 9 | 10 |
| (Operation conditions in 1st cycle) | | | | | | |
| Time of operation for filtering fine crystals [s] | 500 | 500 | 500 | 500 | 120 | 900 |
| Time of back washing operation with filtrate [s] | 15 | 15 | 15 | 15 | 15 | 15 |

TABLE 2-continued

| | | | | | | |
|---|---|---|---|---|---|---|
| Time of back washing operation with wash solvent [s] | 15 | 15 | 10 | 60 | 15 | 15 |
| Circulation of oxidation reaction mother liquor upon back washing operation with wash solvent | Done | Done | Done | Done | Done | Done |
| Feeding linear velocity of wash solvent [m/h] | 2.85 | 5.70 | 8.54 | 1.42 | 2.85 | 2.85 |
| Differential pressure upon back washing with wash solvent [MPa] (Results of operations at 1st cycle) | 0.19 | 0.38 | 0.54 | 0.12 | 0.19 | 0.19 |
| Period of back washing operation with wash solvent [hrs] | 6 | 6 | 6 | 6 | 8 | 3 |
| Filtering flow rate immediately after back washing operation with wash solvent [m³/h] | 0.32 | 0.32 | 0.32 | 0.32 | 0.32 | 0.32 |
| Amount of wash solvent used [m³] | 0.0028 | 0.0057 | 0.0057 | 0.0057 | 0.0028 | 0.0028 |
| Amount of isophthalic acid discarded [%] (Results of operations in 2nd or subsequent cycle) | 0 | 0 | 0 | 0 | 0 | 0 |
| Period of back washing operation with wash solvent [hrs] | 6 | 6 | 6 | 4 | 8 | 3 |

| | Comparative Examples | | Examples | | |
|---|---|---|---|---|---|
| | 5 | 6 | 11 | 12 | 13 |
| (Operation conditions at 1st cycle) | | | | | |
| Time of operation for filtering fine crystals [s] | 500 | 500 | 500 | 500 | 500 |
| Time of back washing operation with filtrate [s] | 15 | 15 | 15 | 15 | 15 |
| Time of back washing operation with wash solvent [s] | 180 | 15 | 180 | 15 | 15 |
| Circulation of oxidation reaction mother liquor upon back washing operation with wash solvent | Not done | Not done | Done | Done | Done |
| Feeding linear velocity of wash solvent [m/h] | 2.85 | 2.85 | 2.85 | 0.59 | 21.4 |
| Differential pressure upon back washing with wash solvent [MPa] (Results of operations at 1st cycle) | 0.19 | 0.19 | 0.19 | 0.09 | 1.06 |
| Period of back washing operation with wash solvent [hrs] | 6 | 6 | 6 | 6 | 6 |
| Filtering flow rate immediately after back washing operation with wash solvent [m³/h] | 0.32 | 0.26 | 0.32 | 0.27 | 0.32 |
| Amount of wash solvent used [m³] | 0.0340 | 0.0028 | 0.0340 | 0.00058 | 0.0213 |
| Amount of isophthalic acid discarded [%] (Results of operations in 2nd or subsequent cycle) | 0.37 | 6.67 | 0 | 0 | 0 |
| Period of back washing operation with wash solvent [hrs] | 6 | 0.5 | 6 | 1 | 6 |

INDUSTRIAL APPLICABILITY

In the filtering operation method according to the present invention, there can be attained such advantages that (1) a filtering operation can be simply performed for a long period of time without clogging of a ceramic filter; (2) no use of a large amount of a wash solvent is needed; and (3) an aromatic carboxylic acid contained in the wash solvent which has been conventionally discarded together with the wash solvent upon cleaning can be recovered. Therefore, it is possible to simplify the operation conditions and improve an output level of an aromatic carboxylic acid upon production of the aromatic carboxylic acid.

EXPLANATION OF REFERENCE NUMERALS

The reference numerals used in FIG. 1, FIG. 2 and FIG. 3 are explained below.

1: Oxidation reaction mother liquor vessel; 2: Pump; 3: Minimum flow line; 4: Control valve; 5: Pressure gauge (P1); 6: Circulation inlet conduit; 7: Filtering module (housing); 8: Ceramic filter; 9: Filtration side; 10: Substrate end surface side; 11: Circulation outlet conduit; 12: Pressure gauge (P2); 13: Control valve; 14: Drain valve; 15: Circulation return conduit; 16: Filtrate outlet conduit; 17: Pressure gauge (P3); 18: Valve; 19: Filtrate vessel; 20: Pump; 21: Minimum flow line; 22: Heat exchanger; 23: Filtrate back washing conduit; 24: Control valve; 25: Control valve; 26: Wash solvent back washing conduit; 27: Heat exchanger; 28: Flow path

The invention claimed is:

1. A filtering operation method for filtering fine crystals contained in an oxidation reaction mother liquor obtained in a process for producing an aromatic carboxylic acid except for terephthalic acid by a cross-flow filtration using a ceramic filter while conducting a flowing circulation operation of the oxidation reaction mother liquor, the method comprising:
   conducting (I) an operation for filtering the fine crystals; and
   conducting (II) a back washing operation with a filtrate while maintaining the flowing circulation operation of the oxidation reaction mother liquor,
   wherein (II) the back washing operation with the filtrate is conducted under the following conditions:
   (II-A) an operation time that is in the range of from 5 to 60 s;
   (II-B) a differential pressure between a filtration side and a flow path side of the ceramic filter which is in the range of from 0.10 to 1.0 MPa;
   (II-C) a feeding linear velocity of the filtrate that is in the range of from 1.0 to 20 m/h; and
   (II-D) a temperature of the filtrate that is in the range of from a temperature of the oxidation reaction mother liquor to a temperature higher by 35° C. than that of the oxidation reaction mother liquor.

2. The filtering operation method according to claim 1, wherein (I) the operation for filtering the fine crystals is conducted under the following conditions:
   (I-A) an operation time thereof that is in the range of from 60 to 1800 s;
   (I-B) a differential pressure between the flow path side and the filtration side that is in the range of from 0.05 to 0.5 MPa;
   (I-C) a circulating linear velocity of the oxidation reaction mother liquor in the flow path of the ceramic filter that is in the range of from 1000 to 10000 m/h as measured at an inlet of the flow path; and
   (I-D) a filtering linear velocity of the filtrate that is in the range of from 0.5 to 3.0 m/h.

3. The filtering operation method according to claim 1, further comprising: conducting (III) a back washing operation with a wash solvent while maintaining the flowing circulation operation of the oxidation reaction mother liquor.

4. The filtering operation method according to claim 3, wherein (III) the back washing operation with the wash solvent is conducted under the following conditions:
   (III-A) an operation time thereof that is in the range of from 5 to 120 s;
   (III-B) a differential pressure between the filtration side and the flow path side upon the back washing operation with the wash solvent that is in the range of from 0.10 to 1.0 MPa;
   (III-C) a feeding linear velocity of the wash solvent upon the back washing operation that is in the range of from 1.0 to 20 MPa; and
   (III-D) a temperature of the wash solvent that is in the range of from the temperature of the oxidation reaction mother liquor to the temperature higher by 35° C. than that of the oxidation reaction mother liquor.

5. The filtering operation method according to claim 3, wherein an operation comprising (I) the operation for filtering the fine crystals and (II) the back washing operation with the filtrate is repeated, and when a flow rate of the filtering operation is not restored by (II) the back washing operation with the filtrate, (III) the back washing operation with the wash solvent is conducted.

6. The filtering operation method according to claim 3, wherein the wash solvent is acetic acid having a water content of from 0.1 to 30% by mass.

7. The filtering operation method according to claim 1, wherein upon the back washing operation with the filtrate, a pressure on a circulation outlet conduit side of the ceramic filter is reduced to produce a differential pressure, thereby feeding the filtrate.

8. The filtering operation method according to claim 1, wherein the aromatic carboxylic acid comprises at least one of benzoic acid, phthalic acid, isophthalic acid, m-toluic acid, trimesic acid, 3,5-dimethyl benzoic acid, trimellitic acid, pyromellitic acid, 1,5-naphthalenedicarboxylic acid and 2,6-naphthalenedicarboxylic acid.

9. The filtering operation method according to claim 1, wherein the filtering operation and the back washing operation are alternately repeated.

10. A method for filtering fine crystals obtained from aromatic carboxylic acid production other than terephthalic acid production, the method comprising:
    maintaining a flowing circulation of an oxidation reaction mother liquor obtained in a aromatic carboxylic acid production other than terephthalic acid production;
    filtering the fine crystals during a filtering operation and utilizing cross-flow filtration with a ceramic filter; and
    back washing with a filtrate during a backwashing operation,
    wherein the back washing operation occurs while maintaining the flowing circulation operation of the oxidation reaction mother liquor and under the following conditions:
    an operation time of from 5 to 60 s;
    a differential pressure between a filtration side and a flow path side that is from 0.10 to 1.0 MPa;
    a feeding linear velocity of the filtrate that is from 1.0 to 20 m/h; and
    a temperature of the filtrate that is between temperature A and temperature B with temperature A being a temperature of the oxidation reaction mother liquor and temperature B being a temperature higher by 35° C. than that of the oxidation reaction mother liquor.

11. The filtering operation method according to claim 10, wherein the filtering operation is conducted under the following conditions:
    an operation time that is in the range of from 60 to 1800 s;
    a differential pressure between the flow path side and the filtration side that is in the range of from 0.05 to 0.5 MPa;
    a circulating linear velocity of the oxidation reaction mother liquor in the flow path of the ceramic filter that is in the range of from 1000 to 10000 m/h at an inlet of the flow path; and
    a filtering linear velocity of the filtrate that is in the range of from 0.5 to 3.0 m/h.

12. The filtering operation method according to claim 10, wherein the filtering operation and the back washing operation are alternately repeated.

* * * * *